(12) United States Patent
Shah et al.

(10) Patent No.: US 10,509,889 B2
(45) Date of Patent: Dec. 17, 2019

(54) DATA PROCESSING SYSTEM AND METHOD FOR COMPUTER-ASSISTED CODING OF NATURAL LANGUAGE MEDICAL TEXT

(71) Applicant: ezDI, Inc., Louisville, KY (US)

(72) Inventors: Nehal Shah, Louisville, KY (US); Amit Sheth, Dayton, OH (US); Shreyansh Bhatt, Vadodara (IN); Raxit Goswami, Vadali (IN); Vatsal Shah, Ahmedabad (IN); Rahil Kanani, Jamnagar (IN); Amrish Patel, Ahmedabad (IN); Parth Pathak, Ahmedabad (IN)

(73) Assignee: ezDI, Inc., Louisville, KY (US)

( * ) Notice: Subject to any disclaimer, the term of this patent is extended or adjusted under 35 U.S.C. 154(b) by 1092 days.

(21) Appl. No.: 14/918,881

(22) Filed: Oct. 21, 2015

(65) Prior Publication Data

US 2016/0132648 A1 May 12, 2016

Related U.S. Application Data

(60) Provisional application No. 62/075,925, filed on Nov. 6, 2014.

(51) Int. Cl.
*G06F 19/00* (2018.01)

(52) U.S. Cl.
CPC ................. *G06F 19/325* (2013.01)

(58) Field of Classification Search
CPC .... G06F 16/367; G06F 19/325; G06F 17/276; G06F 17/2785; G06F 19/00; G16H 10/20; G16H 10/60; G06N 5/02
USPC ........................................ 705/2–3
See application file for complete search history.

(56) References Cited

U.S. PATENT DOCUMENTS

| | | | |
|---|---|---|---|
| 2008/0015418 A1* | 1/2008 | Jarrell | G06Q 50/22 600/300 |
| 2011/0087670 A1* | 4/2011 | Jorstad | G06F 17/277 707/741 |
| 2015/0095016 A1* | 4/2015 | Karres | G06F 17/2785 704/9 |

* cited by examiner

*Primary Examiner* — Joy Chng
(74) *Attorney, Agent, or Firm* — Hill Wallack LLP; Jason L. DeFrancesco

(57) ABSTRACT

A system and method utilizing deep clinical knowledge represented as a knowledge-graph to complement and enhance Natural Language Processing (NLP) for efficient and high-quality computer assisted coding of medical text. One embodiment utilizes the International Classification of Diseases version-10 Procedural Coding System (ICD-10-PCS). The system uses multiple knowledge bases combined with direct mapping provided by the ICD-10-PCS standard to enhance the coverage of assigned code. The system identifies ICD-10-PCS code considering hierarchical mapping and identifies the code by individual ICD-10-PCS character.

9 Claims, 10 Drawing Sheets

FIG. 2

| ROBERT GEORGE | | Issues 0/0 | Summary Sheet | References |
|---|---|---|---|---|
| MRN: 500011, Account Number: 500000011 | | ≡ ICD-10 ▾ | | |

DOCUMENTS | Show: ☑ Coding evidences | ✳

All 39 | Edits 0 | CC/MCC 0 Accepted 0 Modified 0 Rejected 0

Endoscopy/Colonoscopy
Patient Name: GEORGE, ROBERT L.
MRN: 100011
Billing No: 100000011
Admit Date: 01/27/2013
Discharge Date:
Service Date:
Surgery Date: 01/31/2013
ESA Attending Dr:
Report Status:
Extra Copies:
PROCEDURE PERFORMED: *Colonoscopy*
ASSISTANT: None.
ANESTHESIOLOGIST: None.
ANESTHETIC: Fentanyl 50 and Versed 2.
PREOPERATIVE DIAGNOSIS: Hematochezia.
POSTOPERATIVE DIAGNOSIS: Hemorrhoids.
PROCEDURE: The colonoscope was placed in the *rectum* and advanced under visual guidance. Good preparation actually. The cecum was reached. The ileocecal valve and appendiceal orifice were identified. The ascending, transverse, and descending colon was normal. The sigmoid showed a mild amount of diverticular disease, submucosal hemorrhaging; otherwise normal. Coming down to the anal canal, prominent internal hemorrhoids are actually small areas of thrombosis. The endoscope was withdrawn.
IMPRESSION: Hemorrhoid disease, see above, and diverticular disease.

ICD-10-PCS codes →

| K59.00 | Constipation, unspecified |
| --- | --- |
| | *constipation* ▸ | *Constipation* ▸ |

⊕ Add Diagnosis Code

Procedures

| 0DJD8ZZ | Medical and Surgical @ Gastrointestinal System @ Inspection @ Lower Intestinal Tract @ Via Natural or Artificial Opening Endoscopic @ No Device @ No Qualifier |
| --- | --- |
| | *rectum* ▸ | *Colonoscopy* ▸ |

| BF12 | Imaging @ Hepatobiliary System and Pancreas @ Fluoroscopy @ Gallbladder |
| --- | --- |
| | *gallbladder* ▸ | *ERCP* ▸ |

Grouping CMS ver 31.0
DRG: 0, Reimbursement: $0 powered by ezDI

[ LATER ] [ C ]

DATA PROCESSING SYSTEM AND METHOD FOR COMPUTER-ASSISTED CODING OF NATURAL LANGUAGE MEDICAL TEXT

TECHNICAL FIELD

The present disclosure relates to a data processing system and method for clinical knowledge-graph enhanced clinical text natural language understanding for ICD-10-PCS computer-assisted coding of medical text.

BACKGROUND

Assigning pre-specified codes to words and phrases found in a clinical note has been attempted for various coding schemes. International Classification of Diseases version 9 (ICD-9), a coding scheme recommended by the World Health Organization and adopted in USA, is being replaced by a newer version called ICD-10. The ICD-10 coding scheme is a much more detailed coding scheme compared to ICD-9; for this reason, the coding procedure becomes more complex. For healthcare providers, there are about 69,823 diagnostic codes under the new ICD-10-CM (clinical modification) codes, five times more than its predecessor ICD-9-CM. An even more complex matrix of about 71,924 new codes for hospital-based procedures awaits in the ICD-10-PCS (Procedural Coding System), 19 times more codes than ICD-9-CM volume 3. With an increase in the number of concepts, the complexity of automating the identification of coding has also increased.

Another major difference between the ICD-9-CM Procedure and the ICD-10-PCS is structural coherence. While the ICD-9-CM Procedure is flat in its structure, ICD-10-PCS has a multi-axial seven-character alphanumeric code structure (Avril, R F et al., 2011). To address this complexity of medical coding, Computer Assisted Coding (CAC) computer software systems automatically generate a set of medical codes for review/validation and/or use based upon clinical documentation provided by healthcare practitioners.

Natural Language Processing (NLP) and machine learning has been the mainstay of earlier CAC methods such as ICD-9. The new coding scheme of ICD-10-PCS presents challenges such as highly different textual descriptions between the clinical text and the coding descriptions as well as much more fine-grained and multi-layered/multi-level coding structure. Rule-Based NLP systems utilize base dictionaries, which generally do not capture semantic and syntactic variety of entities. Over the years, different research has proven that dictionary-lookup based methods yield no better than 71.5% of F-score (Savova, Guergana K., et al. "Mayo clinical Text Analysis and Knowledge Extraction System (cTAKES): architecture, component evaluation and applications." Journal of the American Medical Informatics Association 17.5 (2010): 507-513). Rule-based methods also depend heavily on syntactic parser accuracy, which is also insufficient for the clinical domain.

SUMMARY

It is difficult to accurately code ICD-10-PCS using only rule-based or only NLP or only machine-learning based approaches because these solutions cannot capture the multi-axial structure of ICD-10, and therefore the solutions that work for the ICD-9-CM procedure do not work for ICD-10-PCS. ICD-10-PCS CAC requires representation of concept class as well as subclasses and/or super classes, relationship between disease to anatomical site, and procedure to anatomical site and medical device. Existing procedures would require trial and error guesswork, which is a time-consuming and inefficient use of computational resources. The present disclosure, however, accomplishes ICD-10-PCS coding using a knowledge base and efficient representation of the same.

ICD-10 requires deep domain knowledge to be represented and used during the coding process. Further, the semantics of the ICD-10 code structure are harder to interpret than the ICD-9 structure. The disclosed, newly developed mapping method for generating a background knowledge base and resulting knowledge base referred to herein as "ezProcOntology" (Procedure ontology with super classes) captures this domain knowledge. Using this knowledge base, the disclosed system directly maps procedures to codes. The knowledge base is represented as a unified graph to represent all the concepts and relationships between these concepts in graphical format. Representing data in the form of a graph and storing it in a graph database enables the system to represent semantics of ICD-10-PCS at the same time it enables efficient graph traversals to support real-time querying with scalability. This increases the coverage as well as precision of the CAC process.

In one embodiment, the present disclosure is directed to a computer-controlled method for analyzing natural language clinical text describing a medical procedure, and for generating an accurate procedure code based on a procedural coding system that associates all known medical concepts to alphanumeric characters in a multi-axial coding structure that prohibits rule-based Natural Language Processing (NLP) and machine learning from generating an accurate procedure code. The procedure code comprises a set of alphanumeric characters corresponding to the described medical procedure. A background knowledge graph is created that models all known medical concepts as nodes in the graph and illustrates hierarchical relationships between the medical concepts. The background knowledge graph is then mapped to the procedural coding system to associate each of the medical concepts with at least one alphanumeric character. The medical text is analyzed to determine key words and phrases identifying medical concepts related to the described medical procedure, and each identified medical concept is mapped to the background knowledge graph to determine each character of the set of alphanumeric characters in the procedure code.

In another embodiment, the present disclosure is directed to a data processing system for analyzing natural language clinical text describing a medical procedure, and for generating an accurate procedure code based on a procedural coding system that associates all known medical concepts to alphanumeric characters in a multi-axial coding structure that prohibits rule-based NLP and machine learning from generating an accurate procedure code. The procedure code comprises a set of alphanumeric characters corresponding to the described medical procedure. The system includes at least one processor coupled to a non-transitory memory that stores computer program instructions, wherein when the at least one processor executes the instructions, the system is caused to: create a background knowledge graph that models all known medical concepts as nodes in the graph and illustrates hierarchical relationships between the medical concepts; map the background knowledge graph to the procedural coding system to associate each of the medical concepts with at least one alphanumeric character; analyze the medical text to determine key words and phrases identifying medical concepts related to the described medical procedure; and map each identified medical concept to the background knowledge graph to determine each character of the set of alphanumeric characters in the procedure code.

In another embodiment, the present disclosure is directed to a non-transitory machine-readable medium having instructions stored therein, which when executed by a processor, cause the processor to perform operations in a data processing system for analyzing natural language clinical text describing a medical procedure, and for generating an accurate procedure code based on a procedural coding system that associates all known medical concepts to alphanumeric characters in a multi-axial coding structure that prohibits rule-based NLP and machine learning from generating an accurate procedure code. The procedure code comprises a set of alphanumeric characters corresponding to the described medical procedure. The operations include: creating a background knowledge graph that models all known medical concepts as nodes in the graph and illustrates hierarchical relationships between the medical concepts; mapping the background knowledge graph to the procedural coding system to associate each of the medical concepts with at least one alphanumeric character; analyzing the medical text to determine key words and phrases identifying medical concepts related to the described medical procedure; and mapping each identified medical concept to the background knowledge graph to determine each character of the set of alphanumeric characters in the procedure code.

All of the disclosed embodiments generate the procedure code without utilizing inefficient, iterative trial-and-error techniques.

BRIEF DESCRIPTION OF THE DRAWINGS

FIG. 2 is an exemplary screenshot of an output of the system;

DETAILED DESCRIPTION

Figure 1:
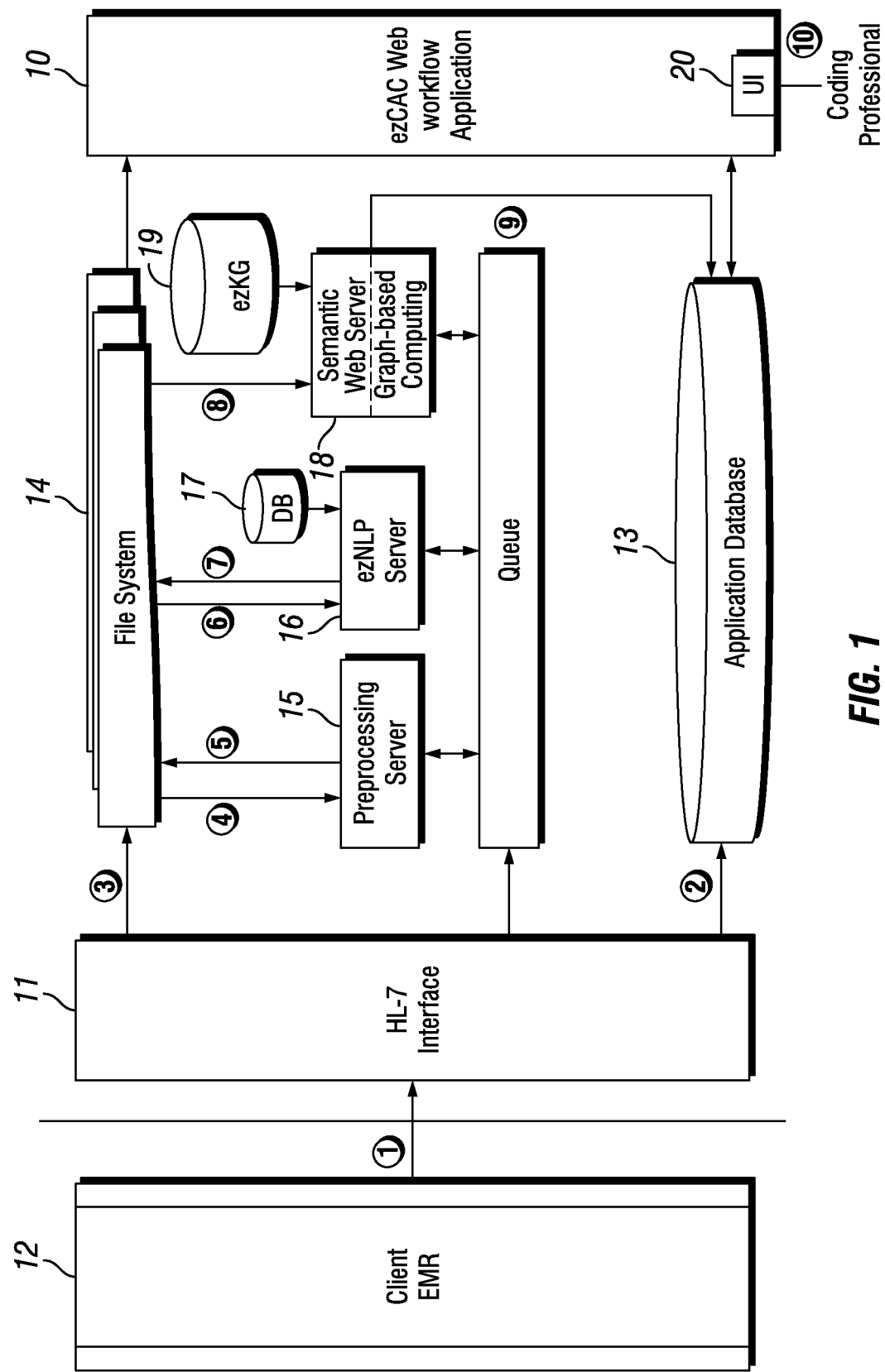
FIG. 1 is a block diagram of an exemplary embodiment of a system for Computer Assisted Coding according to the present disclosure.

FIG. 1 is a block diagram of an exemplary embodiment of a system for Computer Assisted Coding according to the present disclosure. An exemplary method of utilizing the system is shown in the numbered steps and is described in Table 1 below. The block labeled ezKG is the knowledge graph.

TABLE 1

| Steps | Details |
|---|---|
| 1 | Health Level-7 (HL7) Interface 11 receives HL7 Message from client Electronic Medical Record (EMR) 12 |
| 2 | HL-7 Interface parses the HL7 message and stores demographic information into application database 13 |
| 3 | HL-7 interface stores clinical text to file system 14 |
| 4 | Pre-processing server 15 gets text file from file system and starts performing pre-processing |
| 5 | After performing the pre-processing, the preprocessed file is stored into file system 14 |
| 6 | ezDI Natural Language Processing (ezNLP) server 16 gets preprocessed file from file system and starts performing NLP operation using associated database 17 |
| 7 | After performing NLP, XML file is stored into the file system 14 |
| 8 | Semantic web server 18 gets XML file from file system and starts performing graph based computing to find ICD and Current Procedural Terminology (CPT) codes using ezDI knowledge graph (ezKG) 19 |
| 9 | After performing graph based computing, the data is inserted into application database 13 |
| 10 | ezCAC Web Application User Interface (UI) 20 displays suggested codes using associated application database 13 with evidences to a coding professional. |

FIG. 2 is an exemplary screen shot of an output of the system. The system output recommends an ICD-10 code and provides all the evidence for the recommended code to the coding professional.

The system provides a practical solution (via the ezCAC application) to the coding professional. The system uses a unique ezDI knowledge graph and graph-based computing, as described below, to drive better accuracy, coverage, and speed.

Figure 3:
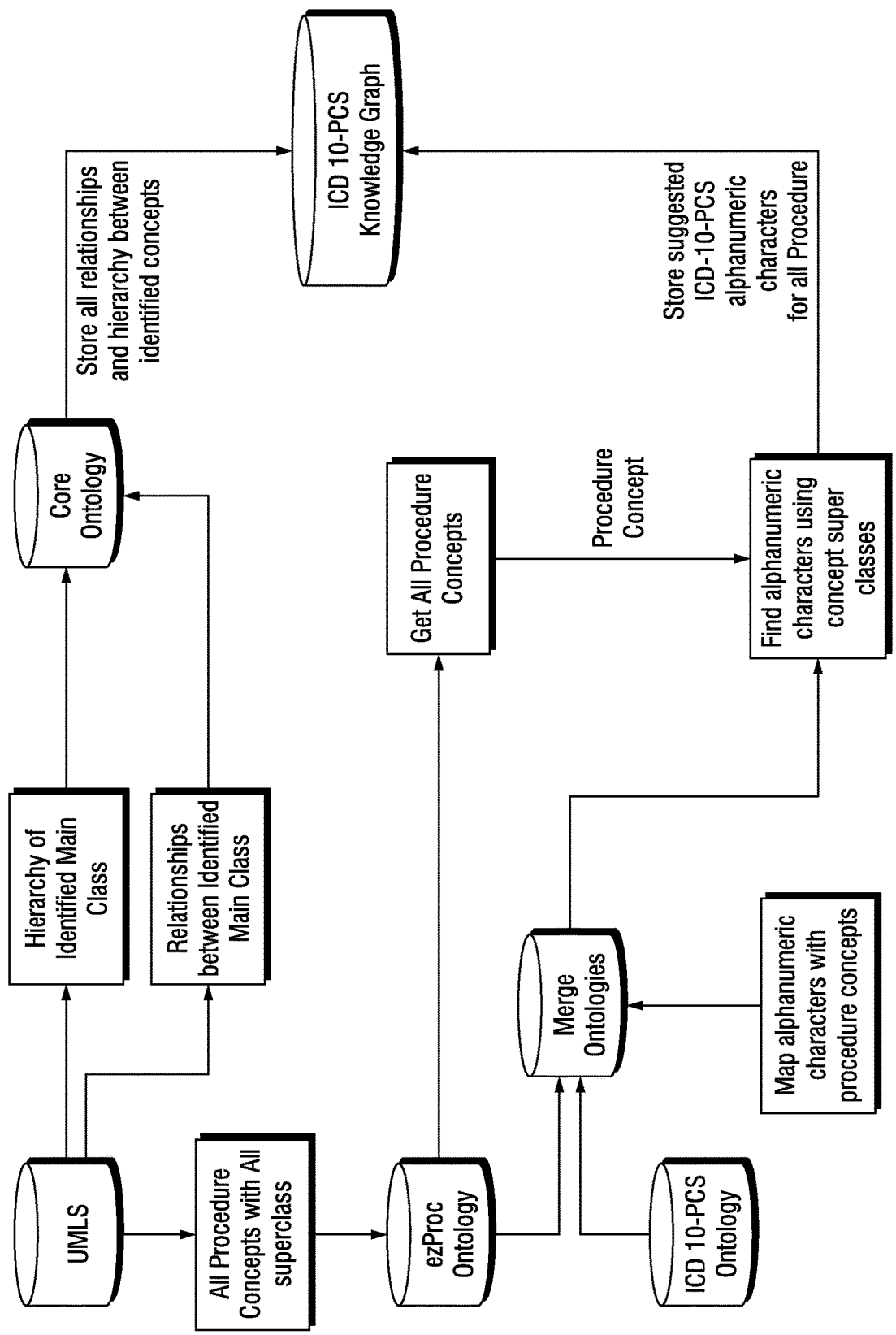
FIG. 3 is a flow chart of an exemplary method of making a knowledge graph for ICD-10-PCS.

FIG. 3 is a flow chart of an exemplary method of making a knowledge graph for ICD-10-PCS. The knowledge graph is developed using three ontologies: "Core ontology" which covers all medical concepts and relationships between those concepts; "Procedure Ontology with all super classes" (ezProcOntology); and "ICD-10-PCS Ontology".

Figure 4:
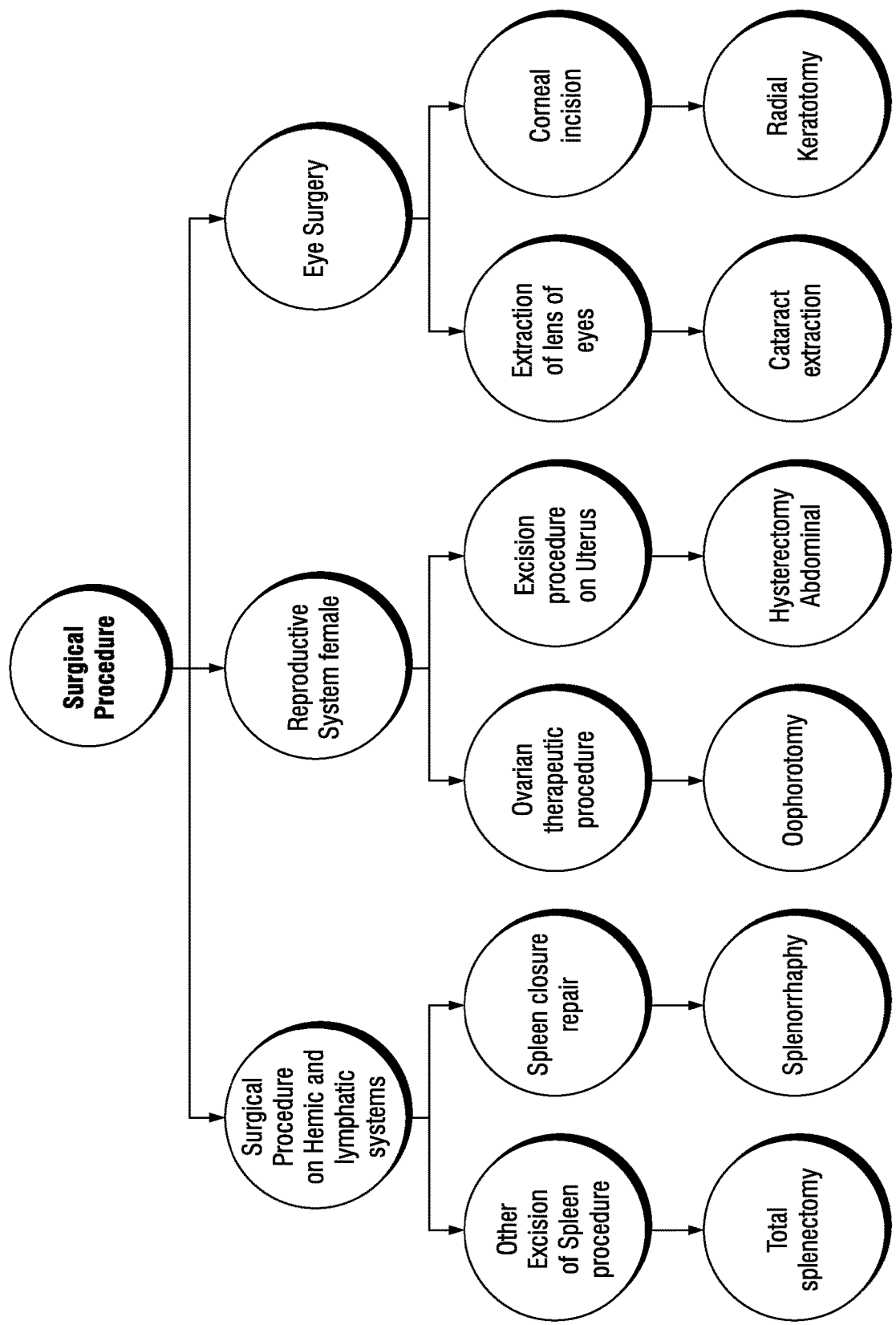
FIG. 4 is an illustration of an exemplary ezProcontology (Procedure ontology with super classes)

FIG. 4 is an illustration of an exemplary ezProcOntology (Procedure ontology with super classes). This ontology provides standardized classification of each procedure with associated super classes, which help to identify Procedure type, body system, root operation, body part, medical device, and approach.

Figure 5:
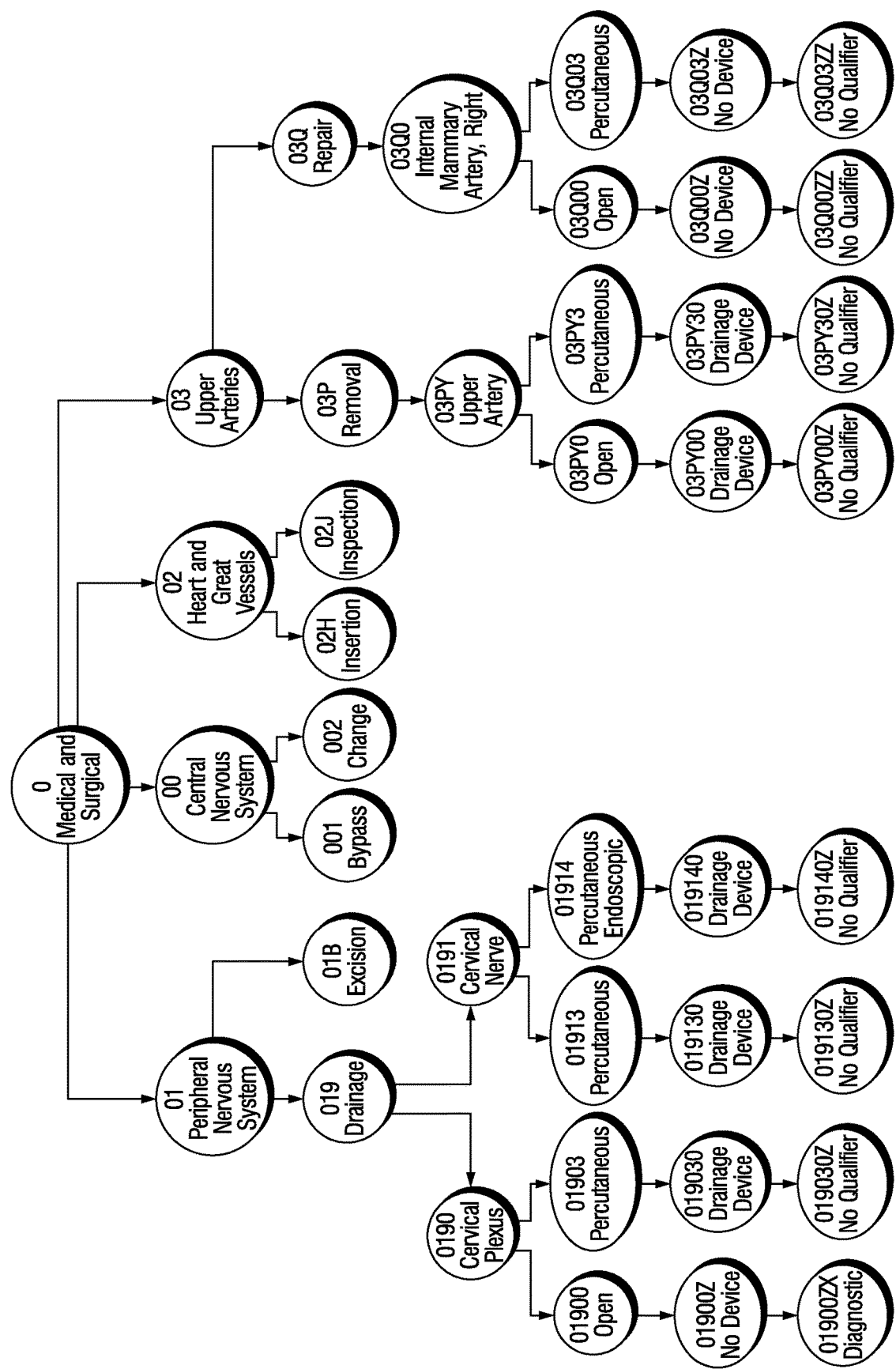
FIG. 5 is an illustration of an exemplary ICD-10-PCS Ontology.

FIG. 5 is an illustration of an exemplary ICD-10-PCS Ontology. ICD-10-PCS Ontology maintains ICD-10-PCS characters hierarchy.

Figure 6:
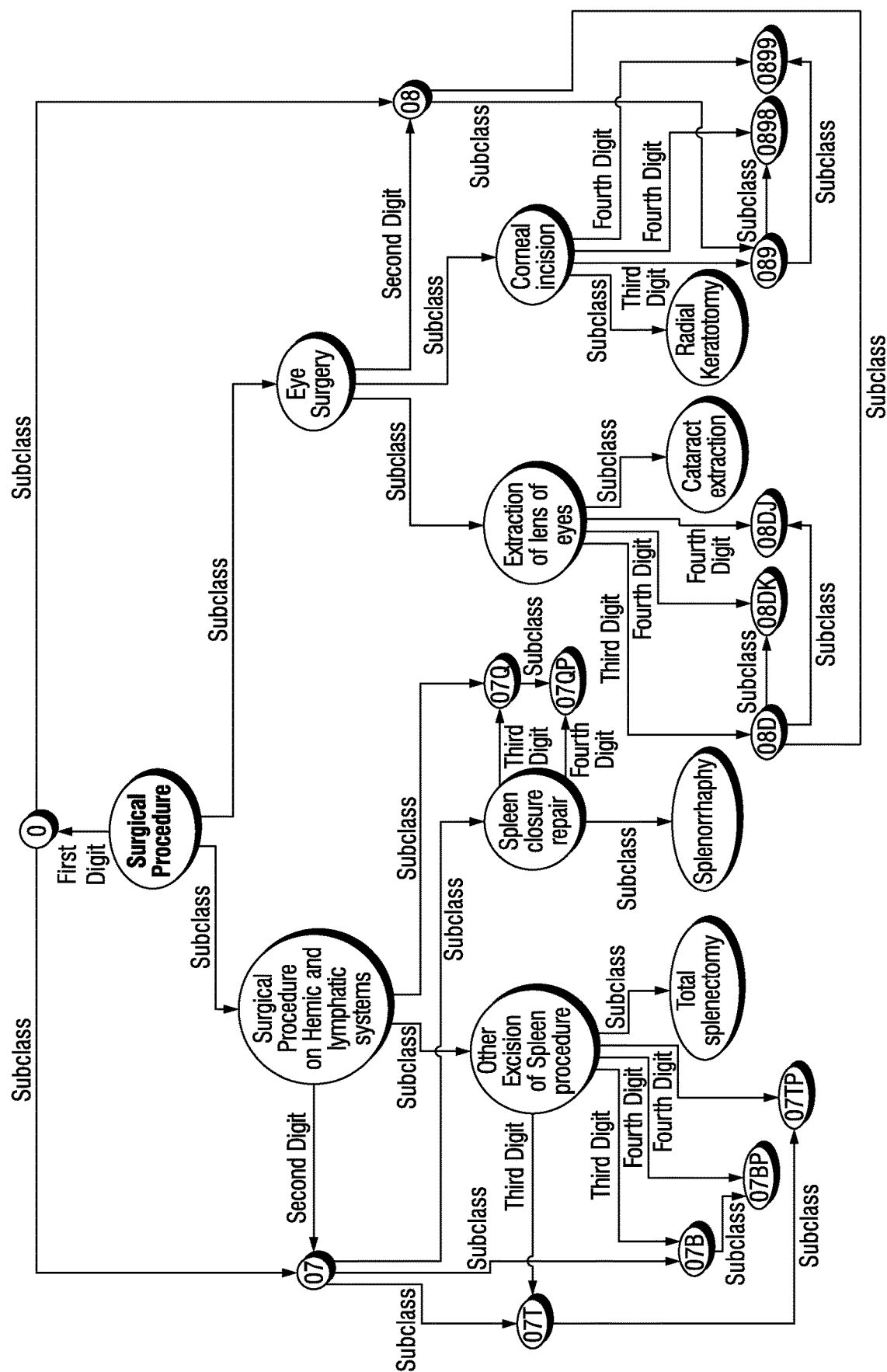
FIG. 6 is an illustration of an exemplary mapping of ezProcOntology with the ICD-10-PCS Ontology.

FIG. 6 is an illustration of an exemplary mapping of ezProcOntology with the ICD-10-PCS Ontology. This figure explains how ICD-10-PCS character description can be mapped to each surgical procedure description, and based on that mapping, it merges ezProcOntology with the ICD-10-PCS Ontology.

Figure 7:
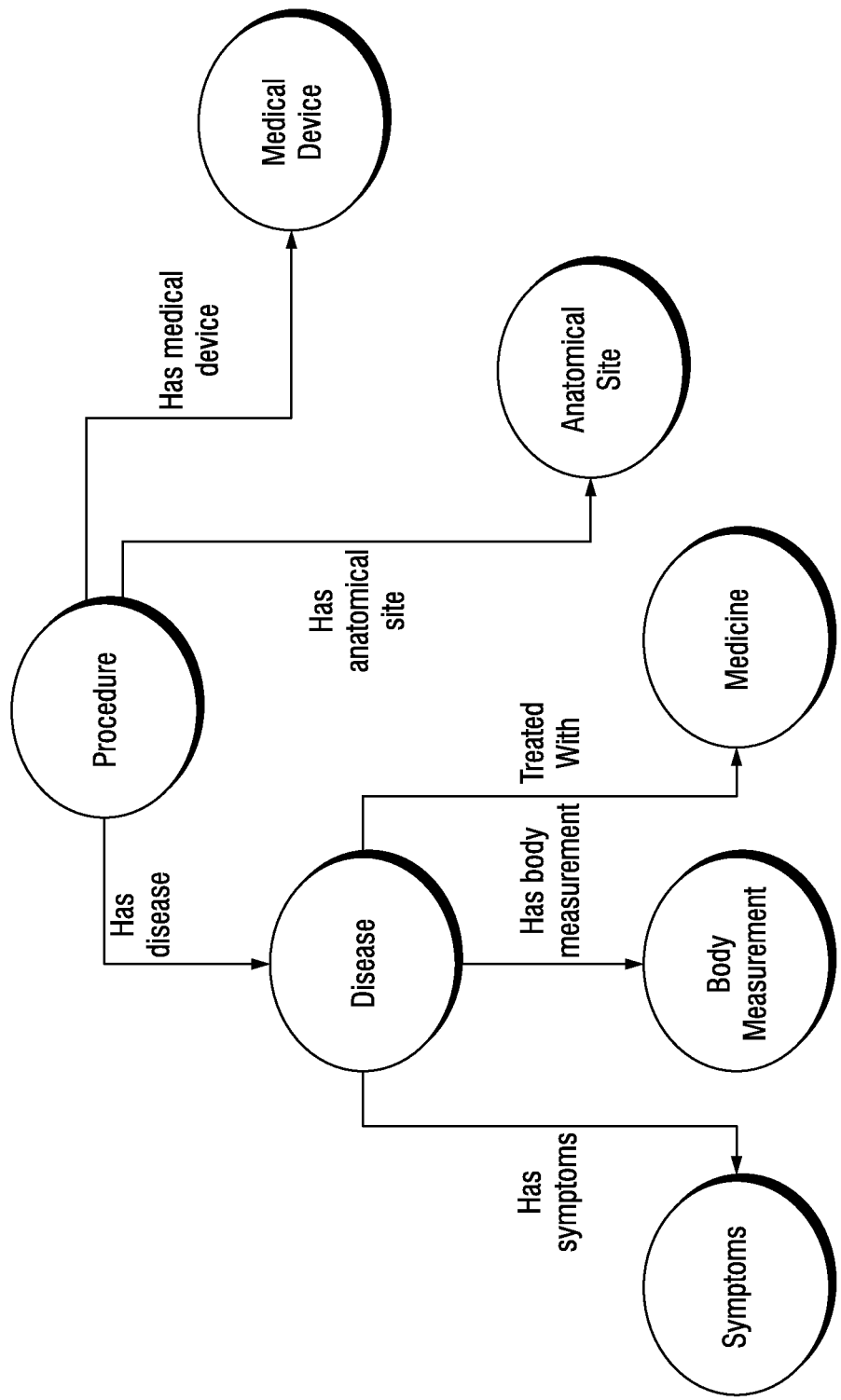
FIG. 7 is an illustration of an exemplary structure of core ontology.

FIG. 7 is an illustration of an exemplary structure of Core ontology. This ontology covers different types of medical concepts with relationships between them such as Diseases, Procedures, Anatomical sites, and the like.

Figure 8:
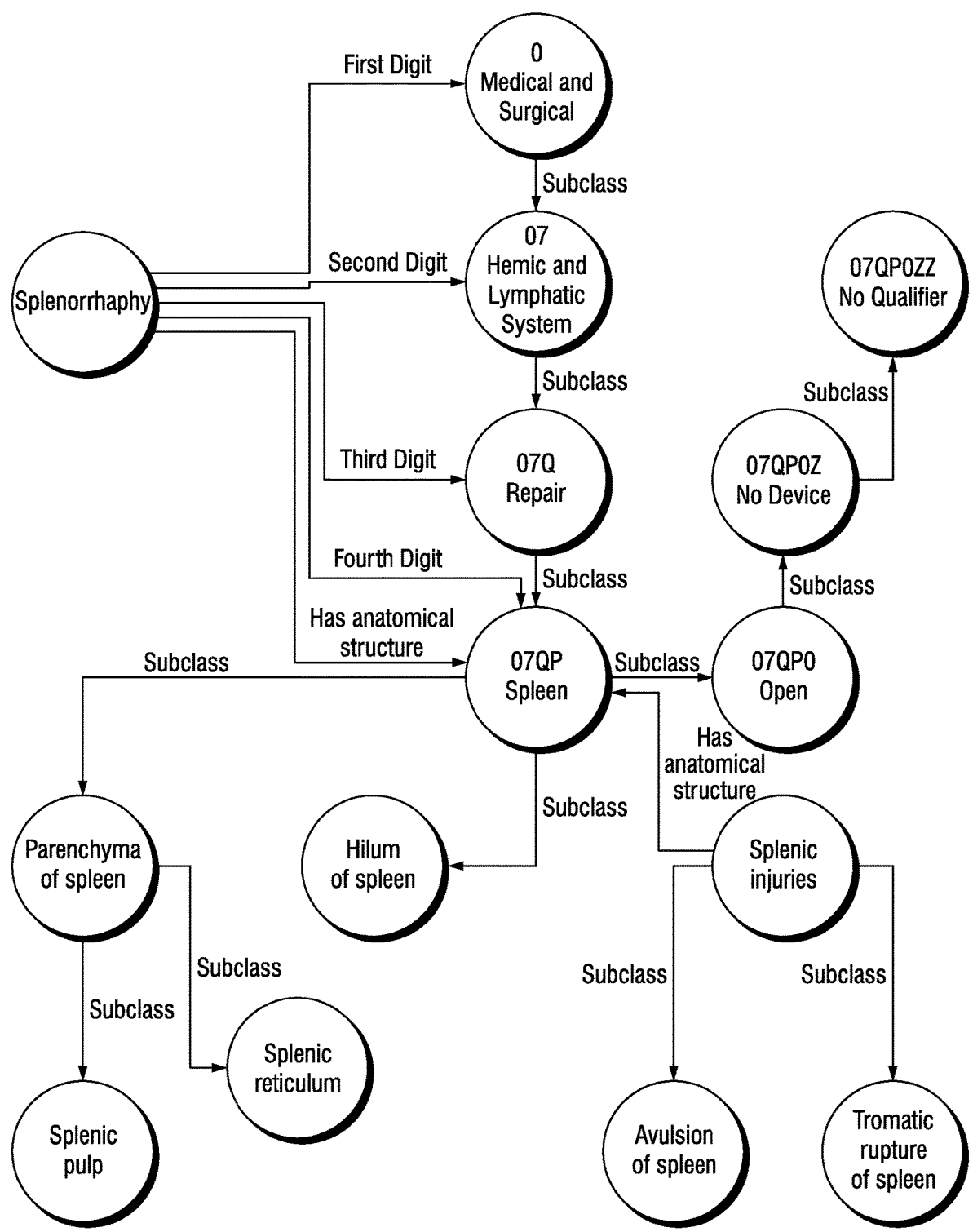
FIG. 8 is an illustration of an exemplary structure of the ezDI Knowledge Graph.

FIG. 8 is an illustration of an exemplary structure of the ezDI Knowledge Graph for procedures concerning the spleen, as an example. This is the development process of the knowledge graph shown in FIG. 3. FIG. 4 shows how the graph looks after inserting the knowledge mapping of ICD-10-PCS.

Figure 9:
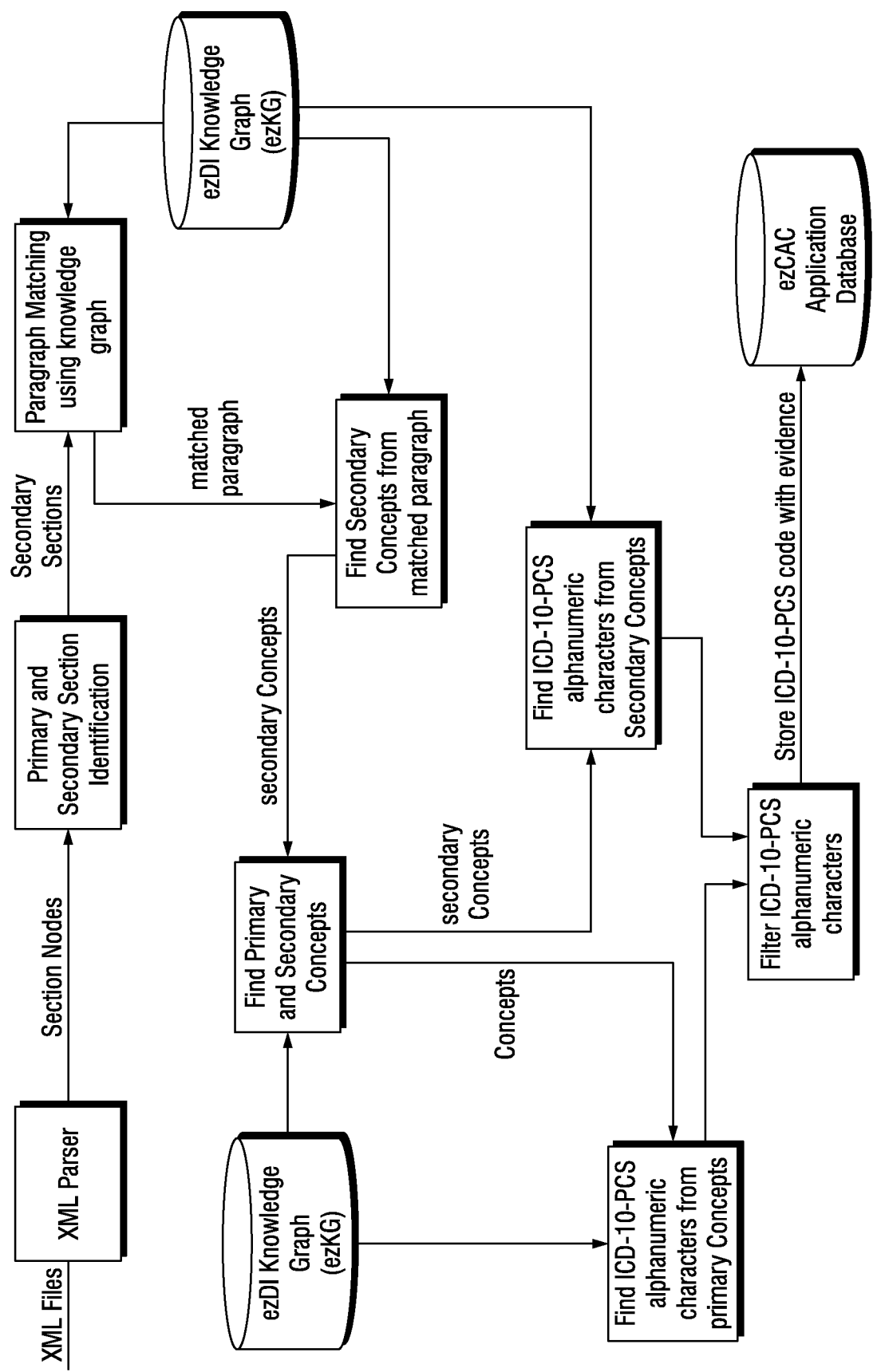
FIG. 9 is a flow chart of an exemplary method of suggesting an ICD-10-PCS code from clinical text.

FIG. 9 is a flow chart of an exemplary method of suggesting an ICD-10-PCS code from clinical text. The input of this method may be formatted, for example, as an XML file. After completion of all steps, the ICD-10-PCS codes may be stored in the application database shown in FIG. 1.

Figure 10:
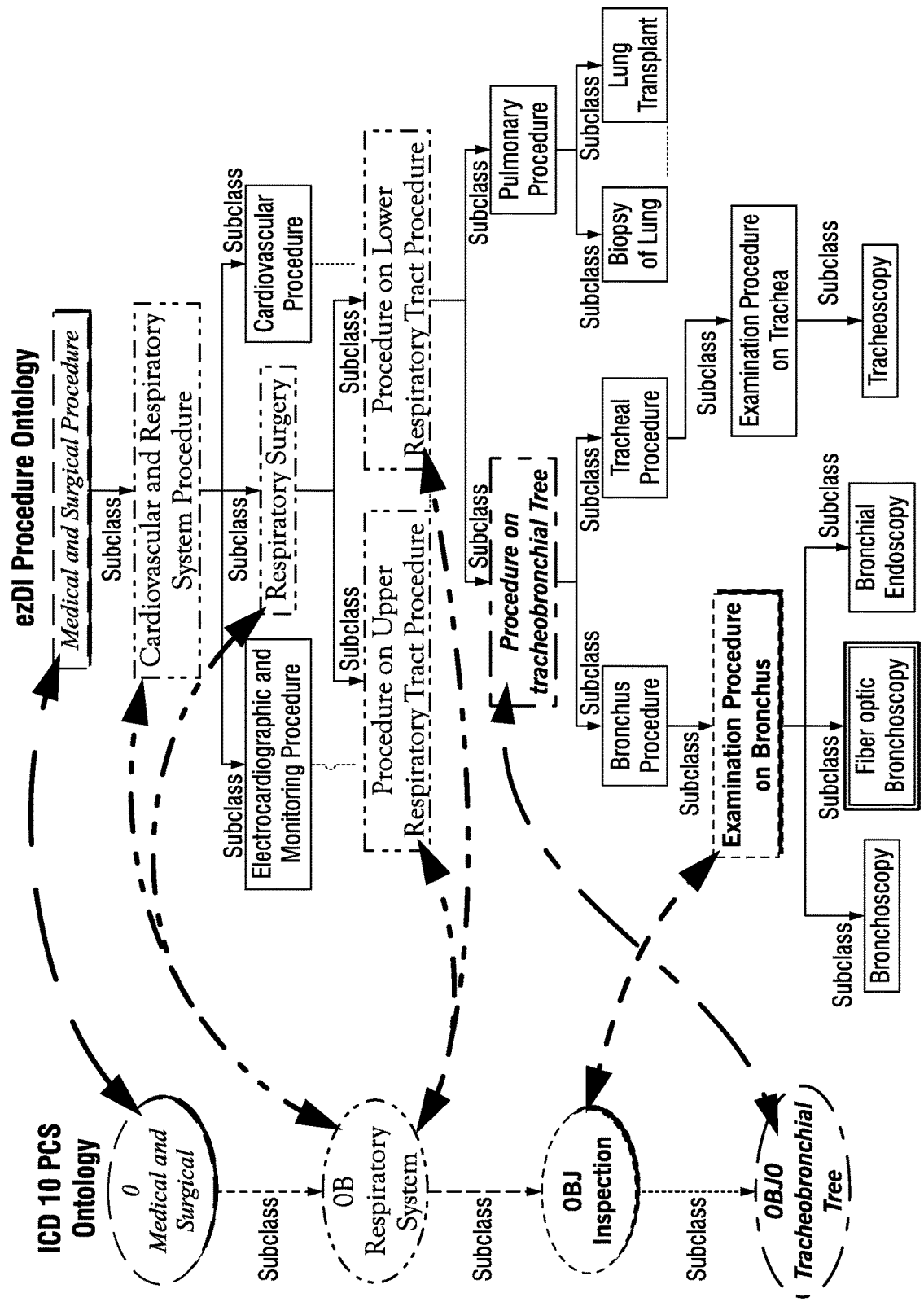
FIG. 10 illustrates an example of the method of suggesting a particular ICD-10-PCS code.

FIG. 10 illustrates an example of the method of suggesting a particular ICD-10-PCS code for the following sample text of a transcribed document:

PROCEDURE PERFORMED: Fiberoptic bronchoscopy

DESCRIPTION OF PROCEDURE: The procedure was performed in the endoscopy suite. The bronchoscope could not be passed easily through either nostril due to narrow nares and the patient's discomfort. No obvious trauma was caused by trying to pass the scope. A bite block was placed and the bronchoscope was inserted orally once sufficient sedation was obtained. The vocal cords were visualized. The patient appeared to have some right true vocal cord weakness. The vocal cords did approximate in the midline. Just below the vocal cords, in the subglottic area, there was scar tissue noted and some mild to moderate narrowing of the upper trachea with almost complete closure of the airway on exhalation. Pictures were taken of the upper trachea, both on inhalation and exhalation. Airways were otherwise quickly examined. The trachea; carina; right upper, middle and lower lobe bronchi; left main stem bronchus and upper and lower lobe bronchi were patent without significant mucosal abnormalities. Other than associated anxiety, the patient tolerated the procedure well maintaining good oxygen saturation during the procedure and was stable. On conclusion, no specimens were collected.

From the sample text mentioned above, the NLP system found the "Fiberoptic Bronchoscopy", "orally", and "endoscopy suit" as evidences from the clinical chart and identified them as primary and secondary evidences to suggest a more specific ICD-10-PCS code. From the "Fiberoptic Bronchoscopy" (Primary Procedure) and secondary evidences, the system suggests "0BJ08ZZ" ICD-10-PCS code.

FIG. 10 shows an exemplary mapping of ICD-10-PCS ontology on the left with ezProcOntology procedures on the right for the sample text mentioned above. Arrows indicate ICD-10-PCS subclasses and associated codes on the left mapped with respective procedures from the ezProcOntology on the right.

Knowledgebase Preparation

The disclosed system uses background knowledge at each level of the multi-axial ICD-10-PCS structure. This knowledge is acquired via various ontologies. The system uses NLP along with ezKG to work in unison with the ICD-10-PCS to automatically generate the relevant code(s). The disclosed solution utilizes a knowledge base comprising three ontologies: Core ontology, which covers all medical concepts and relationships between those concepts; Procedure Ontology with all super classes (ezProcOntology); and ICD-10-PCS Ontology. All these ontologies are combined to prepare a large knowledge base to increase accuracy and coverage. Semantic web technologies are used to address the data integration issue.

The disclosed system generates ICD-10-PCS codes according to the alphanumeric character identified at each level. Different procedure groups in ICD-10-PCS have a base procedure which is referred to as a "super class". From the super classes of procedure, the system can identify top-level ICD-10-PCS layers of the multi-axial structure. For this, an ontology of procedures with all super classes (ezProcOntology) has been developed. Each procedure is represented as a node, and the semantics of each procedure are represented by connecting the procedure with base procedures by an edge in the graph. The system takes all the procedure concepts from the diagnostic, laboratory, and therapeutic procedure groups and obtains all the super classes (base procedure) for every procedure concept. Then a "subClassOf" relationship is assigned between the procedure concepts and their super classes. Finally the system stores all the data into OWL format so that a hierarchy can be maintained and utilized with the other ontologies.

FIG. 4 shows some procedure concepts and their super classes. Super classes of procedure concepts give information about the ICD-10-PCS alphanumeric characters. For example, super classes of "splenorrhaphy" are "spleen closure repair", "surgical procedure on hemic and lymphatic system" and "surgical procedure". Some ICD-10-PCS alphanumeric characters of "splenorrhaphy" can be obtained from the super classes such as the "body part" (in this procedure, "spleen"); "root operation" of this procedure is "repair" from "spleen closure repair" super class; and the "body system" of this procedure is "hemic and lymphatic system" from the "surgical procedure on hemic and lymphatic procedure".

Semantics of each alphanumeric character of ICD-10-PCS codes are captured as part of the ontology, i.e., each character is associated with appropriate procedure concepts. In order to accomplish this, an ontology of ICD-10-PCS hierarchy is created, which also allows the integration of other standard ontologies such as SNOMED. Annotation Process creates relationships between concepts of this ontology and concepts of background knowledge base.

FIG. 5 shows an exemplary ICD-10-PCS ontology where '00', '01', '02' and '03' are the subclass of '0'. In next section the procedure of annotation is illustrated.

One of the challenges in annotation is to ensure the correctness of annotation for this large dataset. To address this, a semi-automatic annotation process has been developed to recognize the correct concept for each respective character as mentioned in the following example (Table 2).

TABLE 2

| ICD-10-PCS Code | Label | And/or grouping |
|---|---|---|
| 0 | Medical and surgical procedure | Medical and/or surgical |
| 09 | Ear, Nose, Sinus | Ear OR Nose OR Sinus |

The following steps are used to annotate ICD-10-PCS characters with procedures from ezProcOntology:

Step 1: Remove common words (surgery, procedure etc.)
Step 2: Convert semantics of an ICD-10-PCS character into a logical expression (see Table 2)
Step 3: Match logical expressions with procedures from ezProcOntology
Step 3a: Direct matching words( )
Example (Shown in FIG. 10 and Table 3):

TABLE 3

| ICD-10-PCS character and Description | Procedure from ezProcOntology |
|---|---|
| 0 - Medical and surgical procedure | Medical and surgical procedures, Surgical procedures |
| 0B - Respiratory System | Respiratory System |
| 0BJ0 - Tracheobronchial Tree | Procedure on tracheobronchial tree |

Step 3b: Direct matching synonyms( )
Example (Shown in FIG. 10 and Table 4):

TABLE 4

| ICD-10-PCS Character and Description | Procedure from ezProcOntology |
|---|---|
| OBJ - Inspection | Examination Procedure on Bronchus |

Step 4: Validate with domain expert
Step 5: Annotation

Proper "and" and "or" grouping is used in order to capture label semantics of each of the alphanumeric characters. In Table 2, to recognize that the characters should be 09, for example, the process may determine whether the procedure super class has any of the terms 'ear' OR 'nose' OR 'sinus'. If the procedure super class has any one of these three terms, it can be mapped with the description of the alphanumeric character. Once the description is identified, the alphanumeric code can be mapped with the procedure super class. It is 09 in this example. At the end of this process, there are mappings between procedure concepts and ICD-10-PCS alphanumeric characters. These two ontologies (ICD-10-PCS and ezProcOntology) are integrated using generated mappings.

From this merged ontology, the system determines ICD-10-PCS characters from the procedure concept. Super classes of the procedure concept are checked and mapped with ICD-10-PCS alphanumeric characters. The relationships of alphanumeric characters to procedure super classes are "has_first_character", "has_second_character", "has_third_character" ... and 'has_seventh_character'. The system may determine multiple first characters using this process, which means multiple main sections are initially determined. To identify the correct main section (ICD-10-PCS first layer), the first characters are ranked. The main section with the highest ranking is considered to be the correct main section.

FIG. 6 shows some procedure concepts and their super classes mapped with the ICD-10-PCS alphanumeric characters.

From the above mapping, the system identifies ICD-10-PCS alphanumeric characters that are identified by only the procedure name. Precise ICD-10-PCS CAC requires not only procedure but also knowledge of other medical concepts like diseases, anatomical structure, symptoms, and medical devices. In addition to this, the system also requires semantics of each concept so as to increase coverage. Core Ontology represents these medical concepts and connects each of them with semantically relevant concepts. However, in order to get more specific ICD-10-PCS code, other evidences have to be considered from the clinical text. These evidences are mapped to the alpha-numeric characters. Concepts that are related to characters are identified using the grouping technique described previously. The system also identifies medical concepts that are related to specific alphanumeric characters. For this, the core ontology of medical domain has been developed.

FIG. 7 shows the structure of the core ontology of the medical domain. The core ontology of the medical domain contains the medical concepts with hierarchy and other domain relationships between:
1) 'Disease' to 'Body Measurement';
2) 'Procedure' to 'Anatomical Site';
3) 'Disease' to 'Medication';
4) 'Disease' to 'Symptoms';
5) 'Medication' to 'Medication' (for contradicted drug);
6) 'Procedure' to 'Medical Device'; and
7) 'Disease' to 'Anatomical Site'.

The system adds these relationships verified by domain experts and subclasses in the knowledge graph to identify more accurate and deeper level alphanumeric characters from the evidences found in the clinical text. Identifying evidence in a clinical document is a challenge because evidences are not mentioned explicitly rather they are in the form of subclass or relationships. For example, if "colon mucosa" or "colitis" is mentioned in the document, this assists the system to determine that these terms are related to colon. This is because "colon mucosa" is the subclass of 'colon' and 'colon' is a 'body part' of disease 'colitis'. Subclass hierarchies and relationships of the background knowledge are used for this purpose.

This data needs to be represented in a way which allows efficient graph traversals. Data is modelled in the form of a graph for these reasons. Each medical concept, ICD-10-PCS code and procedure is represented as a node; these nodes are then connected with appropriate relationships. Thus, a graph is produced which stores procedures, direct mapping of alphanumeric characters as well as semantics, represented by ontologies discussed above. All the knowledge is combined, and a knowledge graph structure is prepared as illustrated in FIG. 8. The process of development of the knowledge graph from the ontologies described above is shown in FIG. 3. Thus the knowledge achieved has the following characteristics:
1) Previously found ICD-10-PCS alphanumeric characters for all procedure concepts;
2) Direct mapping between concepts and ICD-10-PCS alphanumeric characters;
3) Domain Relationship between concepts, which are mentioned in point-2 of this paragraph; and
4) Hierarchy of ICD-10-PCS alphanumeric characters.

Method Overview

First, the disclosed system finds the primary and secondary sections from the section nodes from the XML document, which is the output of the NLP module. The 'section' node is the main header of the documents. Different formats of procedure documents have been analyzed. From the analysis, primary and secondary sections have been identified. The primary section contains the main procedures in the procedure notes while the secondary section contains the descriptions of the main procedures mentioned in the primary sections. Examples are shown in Table 5.

TABLE 5

| Primary Sections | Procedure Performed |
|---|---|
|  | Procedure Title |
|  | Name of Procedure |
| Secondary Sections | Description of procedure |
|  | Procedure in details |

There are some challenges to identify the primary and secondary sections. Procedure documents have some sections like 'procedure', which cannot be distinguished as a primary or secondary section. For this type of problem, the system ranks the sections. An exemplary ranking is shown in Table 6.

TABLE 6

| Rank | Section Name |
|---|---|
| 1 | Procedure Title |
| 2 | Procedure |
| 3 | Procedure In Details |

"Procedure Title" has first rank because procedure title appears in the primary section only. "Procedure" has second rank because procedure comes sometime as primary section and sometime as a secondary section. And "Procedure In Details" has third rank because it always comes as a secondary section. Based on ranking, the problem is solved. For example, two sections may be mentioned in the procedure note such as "Procedure Title" and "Procedure". In this example, "Procedure Title" has highest rank so it becomes a primary section. Likewise, between "Procedure" and "Procedure In Detail", "Procedure" will be the primary section.

Another problem is sections that have the same rank and are mentioned in the same document. The system identifies the section from the content of the sections. Secondary section length is longer than the primary section. Thus sections may be identified using three approaches.

After identifying the sections, the system needs to find primary and secondary concepts using the knowledge base. There is a property named 'primary' in the nodes and the value of this property may be "true" or "false". Stored mappings using 'ezProcOntology' have the value 'true' of 'primary' property. First the system identifies primary procedures from the primary section using a 'primary' property in the knowledge base. The rest of the concepts are considered as evidence of the primary procedures of the same sentence. And there may be other evidences in the secondary section. To find these evidences, the system finds paragraphs mentioned in secondary sections of the primary procedure mentioned in the primary section.

There are two types of sections: primary sections and secondary sections. Primary sections contain only primary procedures. Secondary sections contain a description of the primary procedure. Sometimes there are more paragraphs written in the secondary section, when more procedures are written in the primary section. So the system needs to identify which paragraph is for which primary procedure. Thus, related paragraphs for primary procedures need to be identified.

For document matching, TF-IDF techniques are often used for context matching. This technique, however, is not sufficient in this case. This is concept to paragraph matching that which primary procedure (concept) is related in terms of medical knowledge to which paragraph. And this matching requires domain knowledge. Thus, the system may find the paragraph of the primary procedure using TF-IDF with the background knowledge. Annotation of the procedure with background knowledge helps the system to identify paragraph(s) related to the concept of the primary procedure. Related concepts in the paragraph are considered, which are annotated to the procedure in ezKG. The system identifies the paragraph using the TF-IDF technique based on the related concepts of the primary procedure found in the paragraph. After finding the paragraph, the evidences found in the paragraph are aligned with the primary procedure and move forward for the further process.

The next step is to extract primary and secondary concepts from documents. For example, in FIG. 10, "Fiberoptic bronchoscopy" is the primary concept while "orally" is the secondary concept, which further specifies the code for this procedure. In order to find all the characters of ICD-10-PCS, the algorithm, first finds characters that are associated with the primary concept and then traverses the knowledge graph to find a match for a secondary concept. If a match is found, further ICD-10-PCS characters are determined for this code; otherwise only characters associated with the primary concept are suggested as the final code.

The following filter process is applied to this final code. Secondary concepts can lead to multiple characters. For example, in FIG. 10 the system suggests 0BJ0 ICD-10-PCS code from the procedure name (Fiberoptic Bronchoscopy) itself. From the secondary evidences, "orally" and "endoscopy", the system identifies "Via Natural or Artificial Opening Endoscopic" approach, which is associated with 0BJ08, 0BJ18, 0BJK8 and many more ICD-10-PCS characters. The system determines the specific code for this secondary concept and eliminates the rest of the codes by finding the intersection of the set of ICD-10-PCS characters between these codes and one found from the primary evidence.

As discussed above, to enhance coverage and assign appropriate codes, it is not sufficient to rely on direct mappings, yet direct mappings should be considered first. An object of the present disclosure is to model background knowledge of "procedures and corresponding ICD-10-PCS alphanumeric characters" and direct mappings. Moreover, this knowledge should be stored in a way that reasoning becomes easier on it at the same time it allows efficient direct matching of concepts.

To assign a proper ICD-10-PCS code for a given procedure, it requires finding corresponding ICD-10-PCS characters in the Knowledge base for the given procedure. In other words, the system needs to traverse the knowledge base, which is in the form of a graph. As described above, the system found ICD-10-PCS characters related to primary evidence. From secondary evidences, the system found more specific ICD-10-PCS characters, which are associated with characters found from the primary evidence. Moreover, this traversal should take place in a way that total time to assign the code to a given document does not exceed a threshold of 1-2 seconds. This requirement poses a challenge for using a relational database where traversal of the graph results in a query with many numbers of joins. At the same time, the mapping should be stored in a way that direct matching occurs in almost the same time as in a relational database.

For reasons stated above, the storing scheme in the present disclosure is in the form of a graph, and the system uses a graph database to store this large graph. This facilitates the traversal, and as every node in the graph is indexed, direct matching can be performed in constant time.

FIG. 4 shows an example of the graph being stored in the database. Every concept is a node while these nodes are connected with relationships. Use of the graph database allows the system to store the data in form of a graph structure. In other words, the data are stored in a way that it creates a double link with nodes and relationships to facilitate traversal.

Matching secondary concepts (last step of algorithm) to background knowledge base created, can increase the CAC coverage (recall). This step is modelled as a graph traversal. Specifically, a connectivity query in a graph. The system tries to find whether the secondary concept is connected to a concept (in its subclass hierarchy) which can suggest a code. This connection could even span more than 6-7 hops. The shortest path is considered as the path leading to a code, and paths exceeding a certain threshold value (t=7) are discarded. Since the knowledge graph contains millions of concepts, this query can be very computationally expensive. Hence, specific relationships are used to connect concepts in the graph. This enables the system to reduce the number of nodes to traverse while finding a path between two nodes. In other words, the query is performed over a subgraph consisting of relationship type "subclass".

In summary, the method for automatically suggesting an ICD-10-PCS code for a clinical document develops a knowledge graph that captures a plurality of medical concepts encompassing ICD-10-PCS concepts as well as medical concepts expressed in clinical notes. Background knowledge is used to increase coverage and complement NLP techniques to disambiguate sections of the transcribed document. Digit-based mapping is performed between procedure super classes with ICD-10-PCS alphanumeric characters. A graph data model allows real-time response to queries. A paragraph-matching algorithm is used to execute a procedure using the knowledge base. The system identifies primary and secondary sections from clinical documents.

It is thus believed that the operation and construction of the disclosed system and method will be apparent from the foregoing description. While the system and method shown and described has been characterized as being preferred, it will be readily apparent that various changes and modifications could be made therein without departing from the scope of the invention as defined in the following claims.

What is claimed is:

1. A computer-controlled method for analyzing natural language clinical text describing a medical procedure, and for generating an accurate procedure code based on a procedural coding system that associates all known medical concepts to alphanumeric characters in a multi-axial coding structure that prohibits rule-based Natural Language Processing (NLP) and machine learning from generating an accurate procedure code, wherein the procedure code comprises a set of alphanumeric characters corresponding to the described medical procedure, the method comprising:
    creating a background knowledge graph that models all known medical concepts as nodes in the graph and illustrates hierarchical relationships between the medical concepts;
    mapping the background knowledge graph to the procedural coding system to associate each of the medical concepts with at least one alphanumeric character;
    analyzing the medical text to determine key words and phrases identifying medical concepts related to the described medical procedure; and mapping each identified medical concept to the background knowledge graph to determine each character of the set of alphanumeric characters in the procedure code, wherein the procedure code is generated without utilizing inefficient, iterative trial-and-error techniques;
    wherein creating the background knowledge graph includes mapping medical domain knowledge to ICD-10-PCS concepts to create the knowledge graph, which is utilized as background knowledge for precise ICD-10 Computer Assisted Coding (CAC);
    wherein creating the background knowledge graph includes defining super classes of procedures, and classes and subclasses of procedures within each super class; and
    wherein ICD-10-PCS defines a hierarchy of alphanumeric characters or sets of characters associated with each of the super classes, classes, and subclasses of procedures.

2. The computer-controlled method according to claim 1, wherein the procedural coding system is International Classification of Diseases version 10 Procedural Coding System (ICD-10-PCS).

3. The computer-controlled method according to claim 1, wherein the background knowledge graph represents in graphical format, all known medical concepts related to the described medical procedure, associated medical equipment, and relationships between the procedure and the medical equipment.

4. A data processing system for analyzing natural language clinical text describing a medical procedure, and for generating an accurate procedure code based on a procedural coding system that associates all known medical concepts to alphanumeric characters in a multi-axial coding structure that prohibits rule-based Natural Language Processing (NLP) and machine learning from generating an accurate procedure code, wherein the procedure code comprises a set of alphanumeric characters corresponding to the described medical procedure, the system comprising:
    at least one processor coupled to a non-transitory memory that stores computer program instructions, wherein when the at least one processor executes the instructions, the system is caused to:
    create a background knowledge graph that models all known medical concepts as nodes in the graph and illustrates hierarchical relationships between the medical concepts;
    map the background knowledge graph to the procedural coding system to associate each of the medical concepts with at least one alphanumeric character;
    analyze the medical text to determine key words and phrases identifying medical concepts related to the described medical procedure; and map each identified medical concept to the background knowledge graph to determine each character of the set of alphanumeric characters in the procedure code; wherein the procedure code is generated without utilizing inefficient, iterative trial-and-error techniques;
    wherein the at least one processor is configured to create the background knowledge graph by mapping medical domain knowledge to ICD-10-PCS concepts to create the knowledge graph, which is utilized as background knowledge for precise ICD-10 Computer Assisted Coding (CAC);
    wherein the at least one processor is configured to create the background knowledge graph by defining super classes of procedures, and classes and subclasses of procedures within each super class; and
    wherein ICD-10-PCS defines a hierarchy of alphanumeric characters or sets of characters associated with each of the super classes, classes, and subclasses of procedures.

5. The data processing system according to claim 4, wherein the procedural coding system is International Classification of Diseases version 10 Procedural Coding System (ICD-10-PCS).

6. The data processing system according to claim 4, wherein the background knowledge graph represents in graphical format, all known medical concepts related to the described medical procedure, associated medical equipment, and relationships between the procedure and the medical equipment.

7. A non-transitory machine-readable medium having instructions stored therein, which when executed by a processor, cause the processor to perform operations in a data processing system for analyzing natural language clinical text describing a medical procedure, and for generating an accurate procedure code based on a procedural coding system that associates all known medical concepts to alphanumeric characters in a multi-axial coding structure that prohibits rule-based Natural Language Processing (NLP) and machine learning from generating an accurate procedure code, wherein the procedure code comprises a set of alphanumeric characters corresponding to the described medical procedure, the operations comprising:

creating a background knowledge graph that models all known medical concepts as nodes in the graph and illustrates hierarchical relationships between the medical concepts;

mapping the background knowledge graph to the procedural coding system to associate each of the medical concepts with at least one alphanumeric character;

analyzing the medical text to determine key words and phrases identifying medical concepts related to the described medical procedure; and mapping each identified medical concept to the background knowledge graph to determine each character of the set of alphanumeric characters in the procedure code; wherein the procedure code is generated without utilizing inefficient, iterative trial-and-error techniques;

wherein the operation of creating the background knowledge graph includes mapping medical domain knowledge to ICD-10-PCS concepts to create the knowledge graph, which is utilized as background knowledge for precise ICD-10 Computer Assisted Coding (CAC);

wherein the operation of creating the background knowledge graph includes defining super classes of procedures, and classes and subclasses of procedures within each super class; and wherein ICD-10-PCS defines a hierarchy of alphanumeric characters or sets of characters associated with each of the super classes, classes, and subclasses of procedures.

8. The non-transitory machine-readable medium according to claim 7, wherein the procedural coding system is International Classification of Diseases version 10 Procedural Coding System (ICD-10-PCS).

9. The non-transitory machine-readable medium according to claim 7, wherein the background knowledge graph represents in graphical format, all known medical concepts related to the described medical procedure, associated medical equipment, and relationships between the procedure and the medical equipment.

* * * * *